US006158431A

United States Patent [19]
Poole

[11] Patent Number: 6,158,431
[45] Date of Patent: Dec. 12, 2000

[54] PORTABLE SYSTEMS AND METHODS FOR DELIVERY OF THERAPEUTIC MATERIAL TO THE PULMONARY SYSTEM

[75] Inventor: Trent A. Poole, Amherst, Mass.

[73] Assignee: TSI Incorporated, St. Paul, Minn.

[21] Appl. No.: 09/023,099

[22] Filed: Feb. 13, 1998

[51] Int. Cl.[7] .......................... A61M 15/00; A61M 16/10
[52] U.S. Cl. .............................. 128/203.12; 128/200.16; 128/200.18; 128/200.21; 128/203.26; 128/203.27
[58] Field of Search ........................ 128/200.17, 200.18, 128/200.21, 200.22, 203.12, 203.15, 203.26, 203.27, 200.16, 204.17, 204.25; 604/58; 222/636; 239/338

[56] References Cited

U.S. PATENT DOCUMENTS

| | | | |
|---|---|---|---|
| 4,456,007 | 6/1984 | Nakao et al. ...................... | 128/200.21 |
| 4,649,911 | 3/1987 | Knight et al. ..................... | 128/200.21 |
| 5,277,074 | 1/1994 | Poole et al. . | |
| 5,278,626 | 1/1994 | Poole et al. . | |
| 5,487,378 | 1/1996 | Robertson et al. ................ | 128/200.16 |
| 5,507,277 | 4/1996 | Rubsamen et al. ................ | 128/200.14 |
| 5,522,385 | 6/1996 | Lloyd et al. ...................... | 128/203.26 |
| 5,544,646 | 8/1996 | Lloyd et al. . | |
| 5,551,416 | 9/1996 | Stimpson et al. .................. | 128/200.16 |
| 5,571,246 | 11/1996 | Alldredge ........................... | 128/200.23 |
| 5,586,550 | 12/1996 | Ivri et al. ........................... | 128/200.16 |
| 5,593,390 | 1/1997 | Castellano et al. ..................... | 604/187 |
| 5,596,982 | 1/1997 | Blaha-Schnabel ................. | 128/200.14 |
| 5,641,662 | 6/1997 | Debs et al. . | |
| 5,655,517 | 8/1997 | Coffee . | |
| 5,660,166 | 8/1997 | Lloyd et al. . | |
| 5,687,905 | 11/1997 | Tsai ............................................ | 239/4 |
| 5,694,919 | 12/1997 | Rubsamen et al. ................ | 128/200.14 |
| 5,735,263 | 4/1998 | Rubsamen et al. ................ | 128/200.14 |
| 5,758,637 | 6/1998 | Ivri et al. ........................... | 128/200.16 |
| 5,770,152 | 6/1998 | Schuster et al. .......................... | 422/73 |
| 5,803,362 | 9/1998 | Fraccaroli ............................ | 239/102.2 |
| 5,855,564 | 1/1999 | Ruskewicz .................................. | 604/62 |
| 5,881,716 | 3/1999 | Wirch et al. ....................... | 128/200.16 |
| 5,934,510 | 8/1999 | Anderson .................................... | 222/83 |
| 5,957,124 | 9/1999 | Lloyd et al. ....................... | 128/200.22 |
| 5,971,951 | 10/1999 | Ruskewicz ........................ | 128/200.14 |

OTHER PUBLICATIONS

Pharmaceuticals "'Smart' Device Actuates Metered Dose Inhaler at Best Time for Effective Drug Delivery", 2 pages, date unknown.

Stephen L. Hurst, "Aerosol Device Patents–Yesterday, Today and Tomorrow", Respiratory Drug Delivery V, 1996, p. 195.

Colin W. Pouton et al, "Pharmaceutical and Biopharmaceutical Issues in Gene Delivery to the Lung" Respiratory Drug Delivery V, 1996, pp 33, 34, 40.

John S. Patton, "Deep–Lung Delivery of Therapeutic Proteins", Chemtech 1997, 27(12), pp. 34–38.

*Primary Examiner*—John G. Weiss
*Assistant Examiner*—Joseph F. Weiss, Jr.
*Attorney, Agent, or Firm*—Wolf, Greenfield & Sacks, P.C.

[57] ABSTRACT

A handheld therapeutic material delivery system includes a droplet dispersion chamber, a droplet generating assembly for generating droplets of a fluid containing the therapeutic material and for supplying the droplets to the dispersion chamber, and a gas conditioning assembly for supplying heated gas to the dispersion chamber to form a heated transport gas stream. The droplets are dispersed in the heated transport gas stream in the dispersion chamber to provide an aerosol stream containing the droplets. The aerosol stream is supplied to the patient in response to a negative pressure applied by the patient. The delivery system may include a droplet inspection assembly for determining a characteristic of the aerosol stream and a feedback unit responsive to the determined characteristic of the aerosol stream for controlling one or both of the droplet generating assembly and the gas conditioning assembly.

57 Claims, 8 Drawing Sheets

PORTABLE SYSTEMS AND METHODS FOR DELIVERY OF THERAPEUTIC MATERIAL TO THE PULMONARY SYSTEM

FIELD OF THE INVENTION

This invention relates to systems and methods for delivering therapeutic materials, such as drugs and genetic materials, to the pulmonary system and, more particularly, to systems and methods for delivering therapeutic materials to the pulmonary system with precision control of aerosol droplet size and therapeutic material dosage.

BACKGROUND OF THE INVENTION

Aerosol drug therapy from a liquid solution or suspension containing active ingredients by a jet nebulizer or an ultrasonic nebulizer has been used in hospitals, outpatient clinics and at home. A jet nebulizer uses a high speed air jet, created by compressed air supplied to one or more nozzles, to break a stream of fluid into primary droplets. An ultrasonic nebulizer uses ultrasonic energy to break up a liquid film. The jet or ultrasonic nebulizer is incorporated into an inhaler used to administer medication to the pulmonary system of a patient.

The primary droplets of jet nebulizers have a mean size of between 15 and 500 micrometers, which is reduced to about 1 to 10 micrometers by directing the droplets to impaction baffles. Between 93% and 99% of the generated primary droplets are caught by the baffle system and are returned to the reservoir for continued generation. The droplet size from ultrasonic nebulizers is usually between 5 and 10 micrometers. Nebulization is a dynamic process with continuous changes in total output and droplet size. In continued operation, the solution cools down from room temperature to about 11° C. to 15° C. due to water droplet evaporation. Consequently, concentrations in both the solution and the droplets increase with time. The droplet particle size is sensitive to the ambient temperature, relative humidity and flow rate. These parameters, in turn, affect the evaporation and condensation of water droplets. Loss of droplets in the transport system between the nebulizer and the mouth can be high, depending on the droplet size and the design of the gas flow structure.

It is well known that most commercially available aerosol generating devices do not produce monosize droplets, but a spectrum of polysize droplets. Even the best nebulizers do not always produce a monosize dispersion of liquid droplets. This is especially true in conditions where the orifice used for dropletization becomes contaminated by perimeter surface deposits, such as salts, oils, etc. or by macro particle blockage, such as dirt, fiber etc. All aerosol devices fail when the dropletization nozzle clogs and when the droplet dispersion pneumatics become inadequate.

Researchers are investigating the benefits of a portable, handheld drug delivery system to augment and replace the current CFC based systems which deliver an average aerosol dose of between 30 and 50 micrograms per second. Only a small percentage of the total drug aerosol plume is effectively deposited in the lung. The drug efficacy is controlled by the drug aerosol particle size, with the optimum size being from 1–4 micrometers for deep penetration into the alveolar region within the lungs.

Existing aerosol drug delivery systems have the inherent problem of agglomeration for dry powders and coagulation for droplets. A substantial amount of the aerosolized drug forms larger particles that never reach the critical areas of the lungs. Existing delivery systems do not form monosize particles. Reagglomeration of the drug aerosols produces a broader than predicted particle distribution which, in turn, restricts particle dispersion and promotes variation of deposition pattern in the lungs.

Nebulizers have commonly been utilized for delivery of drugs to the pulmonary system. More recently, aerosolized delivery of genetic material to the pulmonary system has been proposed. U.S. Pat. No. 5,641,662 issued Jun. 24, 1997 to Debs et al discloses methods and compositions for producing a mammal capable of expressing an exogenously supplied gene in cells of the airway. Lipid carrier nucleic acid complexes are prepared and then delivered via aerosol to the lung airway. The methods and compositions are stated to be useful for in vivo gene therapy of pulmonary disorders.

U.S. Pat. No. 5,544,646 issued Aug. 13, 1996 to Lloyd et al and U.S. Pat. No. 5,660,166 issued Aug. 26, 1997 to Lloyd et al disclose systems for the intrapulmonary delivery of aerosolized aqueous formations. These patents describe delivery of an aerosolized drug through a porous membrane.

U.S. Pat. No. 5,278,626 issued Jan. 11, 1994 to Poole et al discloses a system for monitoring and analyzing impurities in a liquid by analyzing the non-volatile residue of droplets of the liquid. The system includes a droplet generator for generating a stream of droplets of the liquid, a droplet inspection unit, a drop-on-demand unit for removing selected droplets from the stream of droplets, a heat exchanger for drying the droplets to provide non-volatile residue particles and a particle size measurement unit.

When treating patients with high potency, toxic drug medications, such as peptides, insulin, oncology treatments, AIDS "cocktail" therapy, etc., or precious, expensive genetic materials, such as for cystic fibrosis, replication defective adenovirus gene therapy, liposome vector gene transfection therapy, cancer therapy etc., there is little margin for dose error due to improper particle size and/or improper dose concentration. Correct particle size and dose concentration are essential for effective lung to bloodstream absorption by the human body. Accordingly, there is a need for improved devices for delivery of drugs and genetic material to the pulmonary system.

SUMMARY OF THE INVENTION

According to a first aspect of the invention, a therapeutic material delivery system is provided. The system comprises a structure defining a droplet dispersion chamber, a droplet generating assembly for generating droplets of a fluid containing the therapeutic material and for supplying the droplets to the dispersion chamber, and a gas conditioning assembly for supplying heated gas to the dispersion chamber to form a heated transport gas stream. The droplets are dispersed in the heated transport gas stream in the dispersion chamber to provide an aerosol stream containing the droplets. The delivery system further comprises a droplet drying tube assembly located downstream of the dispersion chamber for controlled drying of the droplets and for supplying the aerosol stream to a patient in response to a negative pressure applied by the patient, wherein the delivery system is breath actuated. The delivery system is preferably portable and handheld.

The gas conditioning assembly may comprise a gas conduit between an inlet port and the dispersion chamber, and a transport gas heater disposed for heating gas passing through the conduit from the inlet port to the dispersion chamber. The transport gas heater may comprise a heating element and a heat exchanger for coupling thermal energy from the heating element to the gas. The gas conditioning assembly may further comprise a desiccant module disposed in the conduit for absorbing water vapor in the gas passing through the conduit. Thus, the gas conditioning assembly preferably controls the temperature and the relative humidity of the gas supplied to the dispersion chamber. The gas conditioning assembly may comprise a temperature sensor and a relative humidity sensor for sensing the temperature and relative humidity of the gas supplied to the dispersion chamber. The transport gas heater may be controlled in response to the sensed temperature and relative humidity. The conduit may pass through the structure that defines the dispersion chamber, so that the dispersion chamber is heated by the gas passing through the conduit. The dispersion chamber may also be heated by direct thermal contact with the transport gas heater.

The droplet generating assembly may comprise a droplet generator coupled to the dispersion chamber and a fluid feed assembly for supplying the fluid containing the therapeutic material to the droplet generator at a controlled rate. The droplet generator generates droplets of the fluid containing the therapeutic material and supplies the droplets to the dispersion chamber. The fluid feed assembly may comprise means for holding a vial containing the fluid, the vial having a movable piston for forcing the fluid from the vial to the droplet generator, and a piston driver for controlled displacement of the piston. The droplet generator may comprise a nozzle having one or more orifices for supplying the fluid containing the therapeutic material and a piezoelectric driver for oscillating the nozzle. The droplet generator may be configured such that the nozzle is easily replaceable after each dose application. Other configurations of the fluid feed assembly and the droplet generator may be used within the scope of the invention.

The droplet drying tube assembly is preferably pivotable between an operating position in alignment with the dispersion chamber and a storage position. The drying tube assembly may be affixed to a pivotable hub that closes the dispersion chamber when the drying tube is in the storage position. The drying tube assembly may have a fixed length or a telescoping structure. The drying tube assembly is easily removable for maintaining cleanliness and so that the system may be used by different patients. The delivery system may be deenergized when the drying tube assembly is in the storage position.

According to another aspect of the invention, a therapeutic material delivery system is provided. The delivery system comprises a structure defining a droplet dispersion chamber, a droplet generating assembly for generating droplets of a fluid containing the therapeutic material and for supplying the droplets to the dispersion chamber, and a gas conditioning assembly for supplying a gas to the dispersion chamber to form a transport gas stream. The droplets are dispersed in the transport gas stream in the dispersion chamber to provide an aerosol stream containing the droplets. The delivery system further comprises a droplet inspection assembly for determining a characteristic of the aerosol stream, and a feedback unit responsive to the determined characteristic of the aerosol stream for controlling one or both of the droplet generating assembly and the gas conditioning assembly.

In a first embodiment, the droplet inspection assembly includes means for determining the sizes of the droplets in the aerosol stream and the feedback unit includes means for controlling one or both of the droplet generating assembly and the gas conditioning assembly in response to the determined sizes of the droplets.

In a second embodiment, the droplet inspection assembly includes means for determining droplet concentration in the aerosol stream and the feedback unit includes means for controlling one or both of the droplet generating assembly and the gas conditioning assembly in response to the determined droplet concentration.

In a third embodiment, the droplet inspection assembly includes means for determining a droplet rate of the droplets in the aerosol stream and the feedback unit includes means for controlling one or both of the droplet generating assembly and the gas conditioning assembly in response to the determined droplet rate.

In a fourth embodiment, the droplet inspection assembly includes means for determining composition of the therapeutic material. The means for determining composition may include means for illuminating the droplets in the aerosol stream with a light beam of a first wavelength and means for sensing florescence emissions from the therapeutic material at one or more second wavelengths.

In a fifth embodiment, the droplet inspection assembly includes an image sensor for obtaining an image of the aerosol stream and means for determining a characteristic of the aerosol stream from the image. One or both of the droplet generating assembly and the gas conditioning assembly may be controlled in response to the determined characteristic.

In a sixth embodiment, the droplet inspection assembly includes means for determining a characteristic of the aerosol stream from light scattered by the aerosol stream. One or both of the droplet generating assembly and the gas conditioning assembly may be controlled in response to the determined characteristic.

According to a further aspect of the invention, a method for delivering a therapeutic material to the pulmonary system of a patient is provided. The method includes the steps of heating a gas, forming the heated gas into a heated transport gas stream, dispersing droplets of a fluid containing the therapeutic material in the heated transport gas stream to form an aerosol stream, controllably drying the droplets in the aerosol stream and delivering the aerosol stream to the patient after the step of controlled drying thereof, in response to inhalation by the patient.

According to yet another aspect of the invention, a method for delivering a therapeutic material to the pulmonary system of a patient is provided. The method includes the steps of providing a transport gas stream, dispersing droplets of a fluid containing the therapeutic material in the transport gas stream to form an aerosol stream, determining a characteristic of the aerosol stream and controlling generation of the aerosol stream in response to the determined characteristic.

Another aspect of the invention is the unique ability to target designated regions of the pulmonary system for site-specific deposition of aerosol droplets containing therapeutic material. This feature is controlled by the inspection assembly and the feedback unit, whereby a droplet size distribution and generation period are predetermined.

Another aspect of the invention is the unique ability to control aerosol droplet size in near real time. This provides this therapeutic material delivery system with unparalleled "payload versatility", which is the ability to deliver varying amounts of therapeutic material over a broad dynamic range using the same delivery system.

BRIEF DESCRIPTION OF THE DRAWINGS

For a better understanding of the present invention, reference is made to the accompanying drawings, which are incorporated herein by reference and in which.

DETAILED DESCRIPTION

The present invention relates to a device capable of generating and delivering to the pulmonary system of a patient a narrow particle spectrum from dried droplets of drug solution or a specified aerosol droplet size of genetic material. The delivery device is preferably implemented in a portable, handheld configuration. The delivery system may be equipped with an onboard aerosol inspection assembly capable of: 1) analyzing aerosol droplet size and taking corrective action, 2) analyzing aerosol concentration and taking corrective action, and/or 3) autocalibrating the droplet inspection assembly prior to each aerosol medication use.

The delivery system of the invention ensures that a patient is medicated properly and safely. If the system is malfunctioning, the system automatically shuts down before administering an inadequate, toxic or lethal dose of therapeutic material. The ability to deliver an accurately measured dose of therapeutic material is particularly important with children and diseased persons because of their physiological inability to tolerate drug overdoses.

Monosize droplets form a precise monodispersion aerosol of powdered drug material after the droplet liquid has evaporated. The resulting aerosol is comprised of particles that relate to the droplet size by a concentration function: diameter cubed of the particle divided by the diameter cubed of the droplet. Two major benefits are obtained from this change of state from larger liquid droplets to smaller drug particles. First the droplets are readily transported because of their greater inertial mass and aerodynamic size. Second, the resulting dried crystalline drug pellets can be produced small enough (1–4 micrometers) to be targeted to the deep lung for direct absorption into the bloodstream, or may be targeted to other regions of the pulmonary system based on designated particle size.

Figure 1:
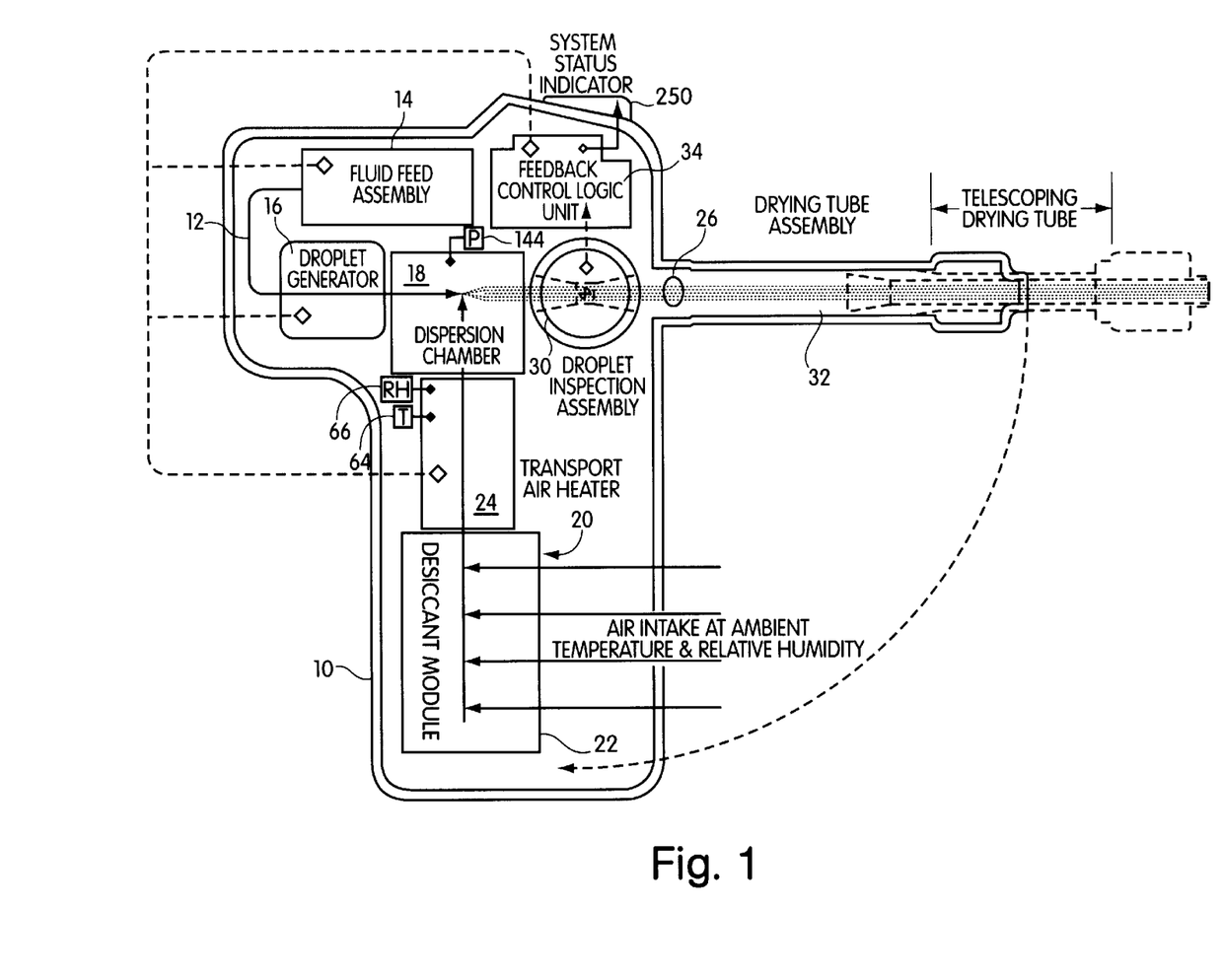
FIG. 1 is a pictorial block diagram of a therapeutic material delivery system in accordance with an embodiment of the invention.

A simplified pictorial block diagram of an embodiment of the therapeutic material delivery system is shown in FIG. 1. A compact handheld housing 10 encloses the components of the delivery system. A droplet generating assembly 12 includes a fluid feed assembly 14 and a droplet generator 16. The fluid feed assembly 14 supplies a fluid to the droplet generator 16. The fluid contains the drug or genetic material to be administered to the patient. The droplet generator 16 supplies precisely controlled droplets to a droplet dispersion chamber 18. A gas conditioning assembly 20 includes a desiccant module 22 and a transport air heater 24. The gas conditioning assembly 20 receives ambient air and supplies air that has been heated, dried and filtered to dispersion chamber 18 as a heated transport gas stream. The droplets from droplet generator 16 are dispersed in the transport gas to form an aerosol stream 26. The aerosol stream 26 passes through a droplet inspection assembly 30 and a drying tube assembly 32 for delivery to a patient.

The droplet inspection assembly 30 determines one or more characteristics of aerosol stream 26. A feedback unit 34 controls operation of one or more of fluid feed assembly 14, droplet generator 16 and transport air heater 24, as described in detail below.

The drying tube assembly 32 promotes controlled drying of the droplets in the aerosol stream by the heated transport gas. The amount of drying is determined by the temperature and relative humidity of the transport air and by the sizes of the droplets, as well as the length of the drying tube assembly 32.

The patient places the drying tube assembly 32 in his or her mouth and inhales. Inhalation by the patient produces in the dispersion chamber 18 a negative pressure which activates operation of the delivery system by mechanical switching or electronic sensing. When the patient stops inhaling, the pressure in the dispersion chamber 18 rises and delivery of the aerosol stream is inhibited. Thus, the delivery system is breath activated for aerosol medication on demand.

Figure 2:
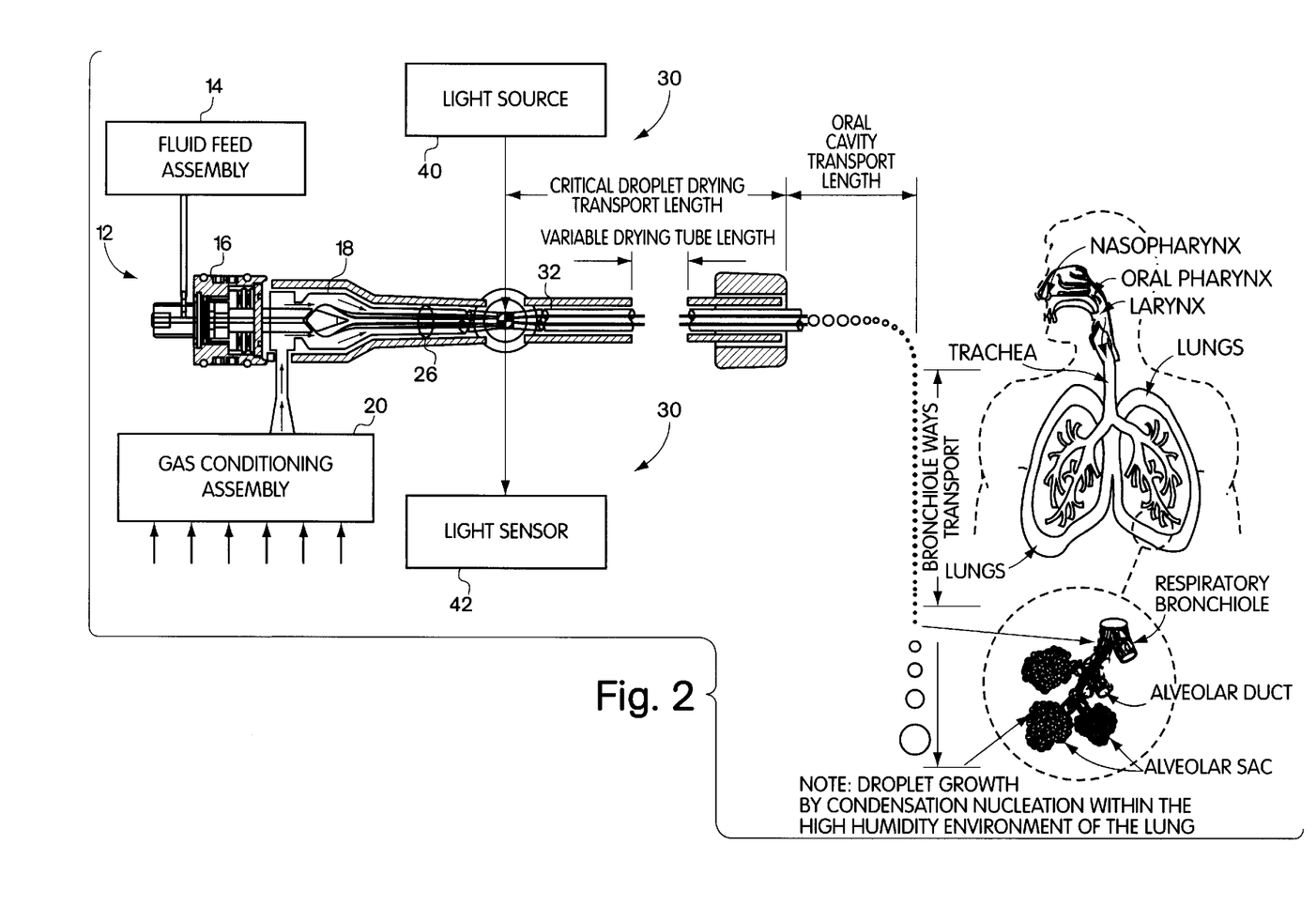
FIG. 2 is a schematic block diagram of the therapeutic material delivery system, illustrating delivery of therapeutic material to the pulmonary system of a patient.

A schematic representation of the therapeutic material delivery system of the invention is shown in FIG. 2. Droplets from droplet generator 16 are dispersed in the dried and heated transport gas stream in dispersion chamber 18 to form aerosol stream 26. The aerosol stream 26 passes through droplet inspection assembly 30 and drying tube assembly 32. Droplet inspection assembly 30 may, for example, include a light source 40 which directs a light beam through aerosol stream 26 to a light sensor 42. The sensed light beam is indicative of one or more characteristics of aerosol stream 26. In drying tube assembly 32, partial or complete drying of the droplets in aerosol stream 26 is produced by the heated transport gas. As indicated in FIG. 2, the droplets continue drying as they pass through the pulmonary system of the patient.

The final deposition site is determined in part by the sizes of the droplets and/or therapeutic material particles. Smaller droplets and/or particles are deposited more deeply in the patient's lungs. By precisely controlling the droplet or particle size, the deposition site can be controlled. By providing droplets or particles within a narrow range of sizes, a larger proportion of the total dose of therapeutic material is delivered to the target site.

Figure 3:
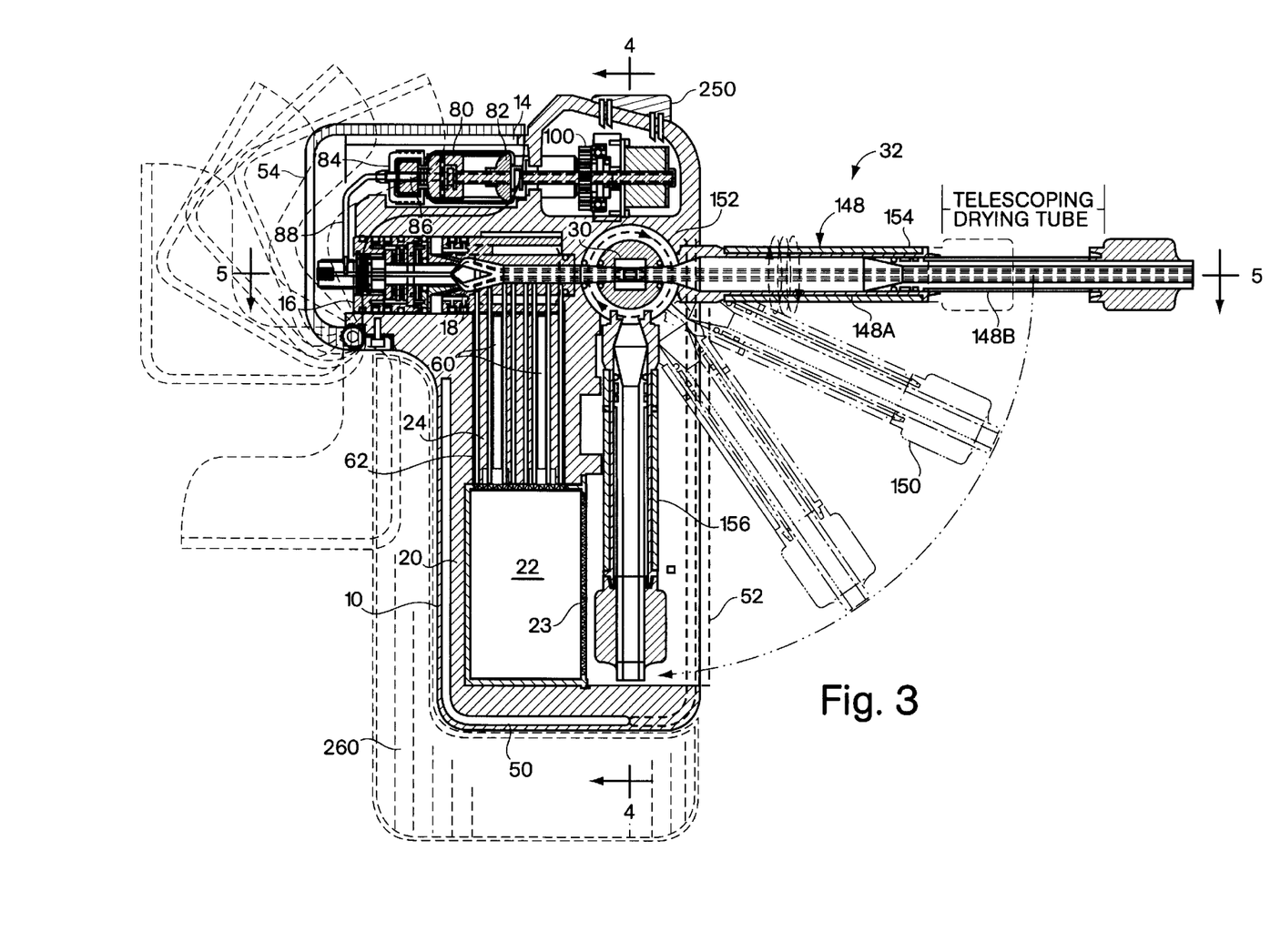
FIG. 3 is a cross-sectional elevation view of an example of an implementation of the therapeutic material delivery system of the invention.
Figure 4:
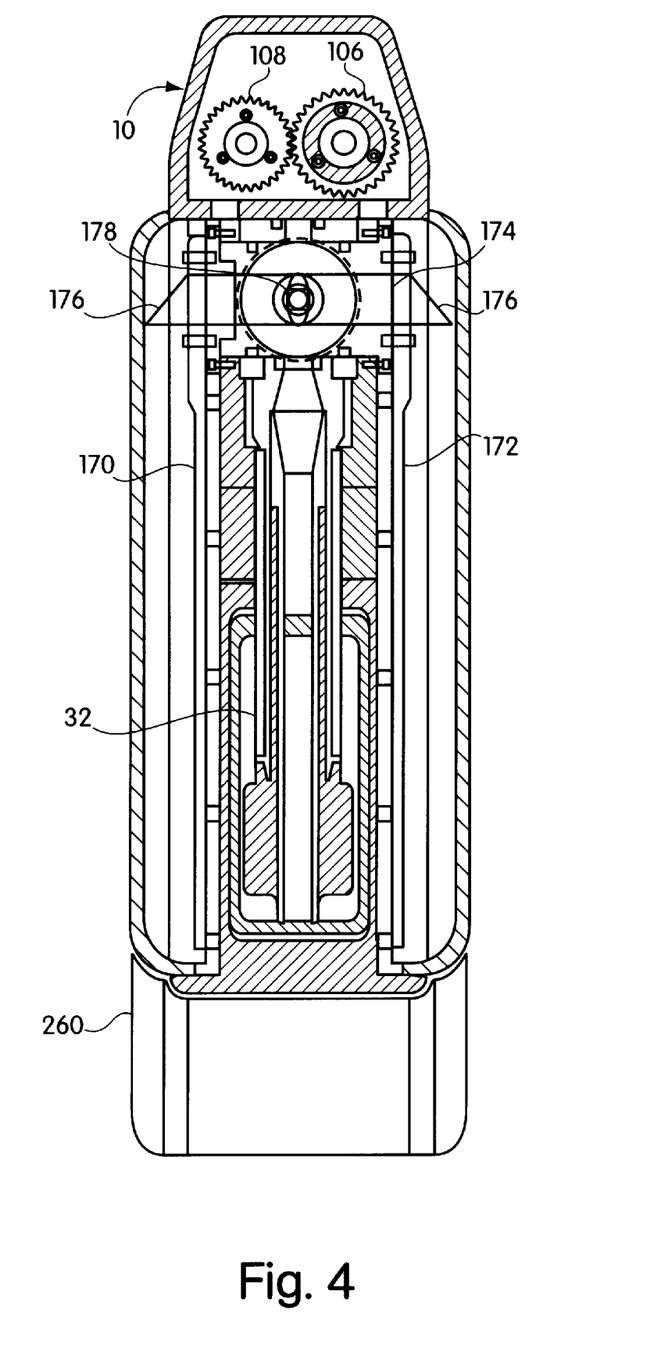
FIG. 4 is a cross-sectional elevation view of the therapeutic material delivery system, taken along the line 4—4 of FIG. 3.
Figure 5:
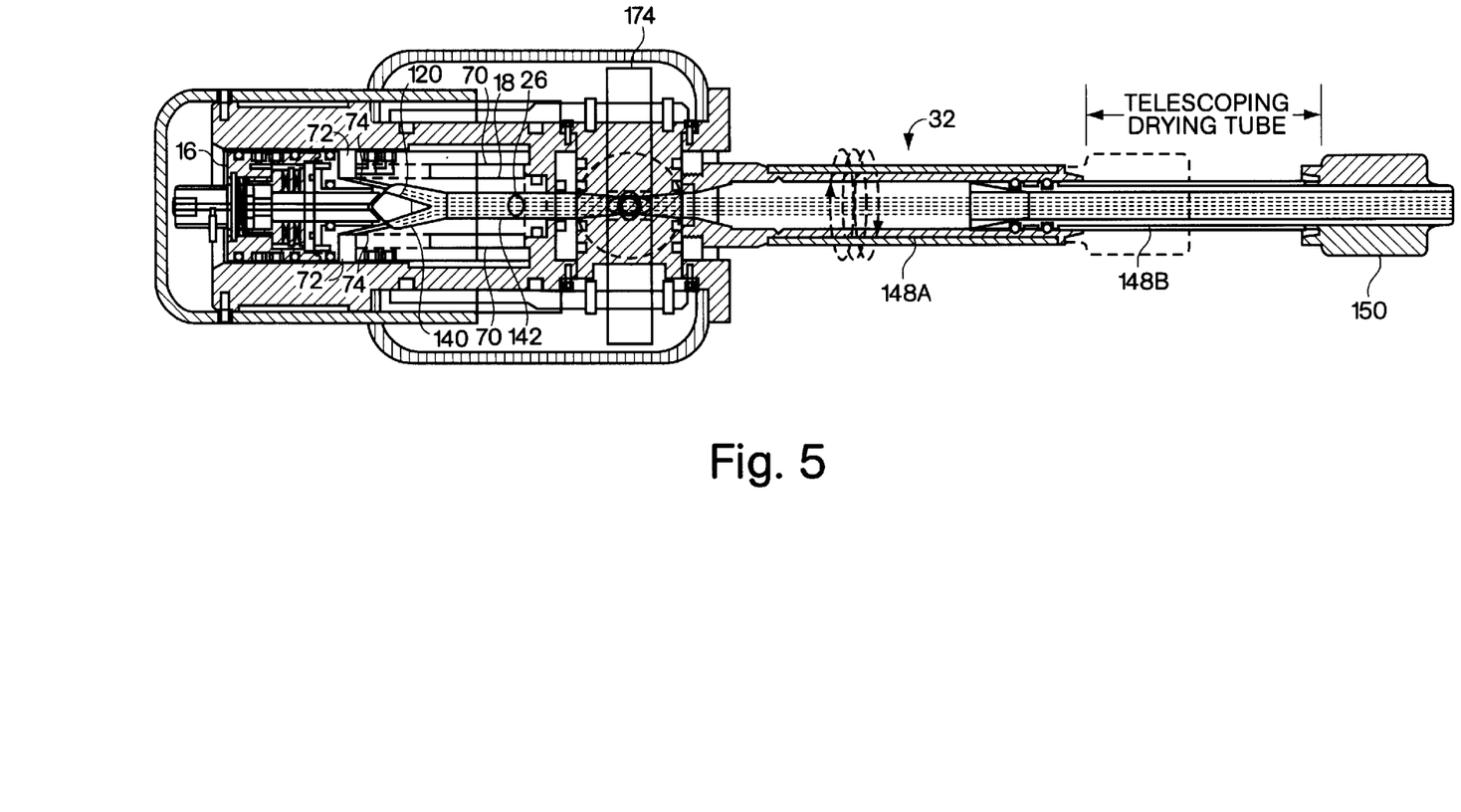
FIG. 5 is a cross-sectional top view of the therapeutic material delivery system, taken along the line 5—5 of FIG. 3.
Figure 6:
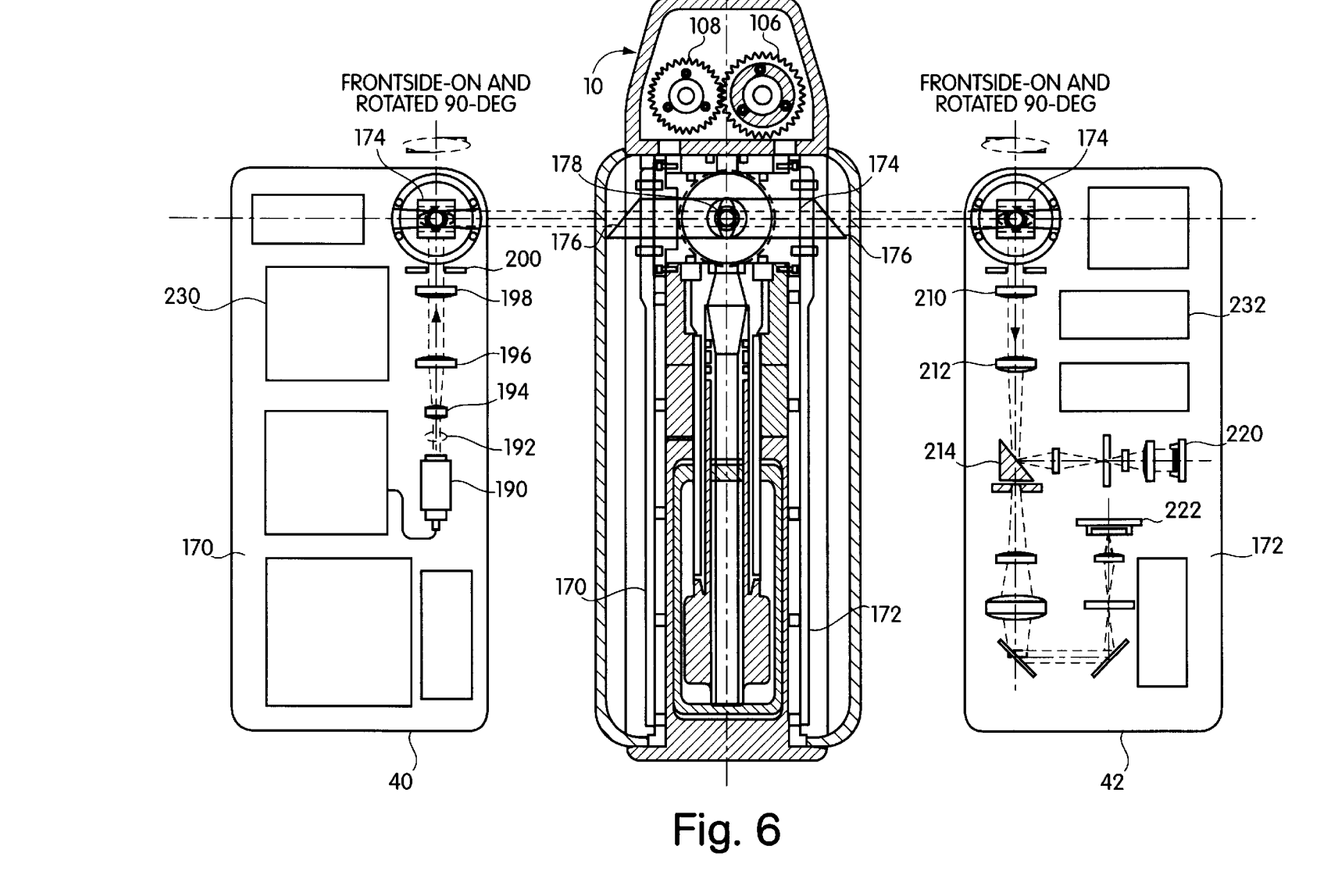
FIG. 6 is a cross-sectional elevation view of the therapeutic material delivery system, with printed circuit boards and optical components of the droplet inspection assembly shown schematically for illustrative purposes.
Figure 7:
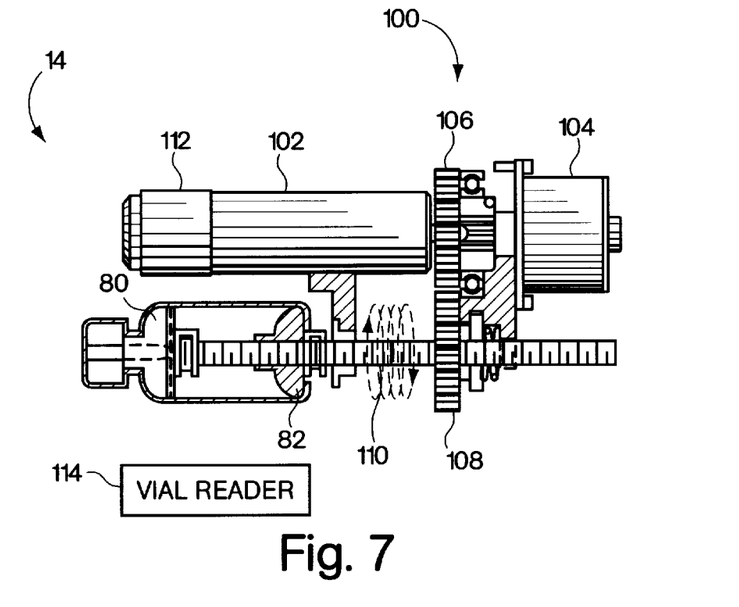
FIG. 7 is a top view of an example of a fluid feed assembly that may be used in the therapeutic material delivery system of FIG. 3.
Figure 8:
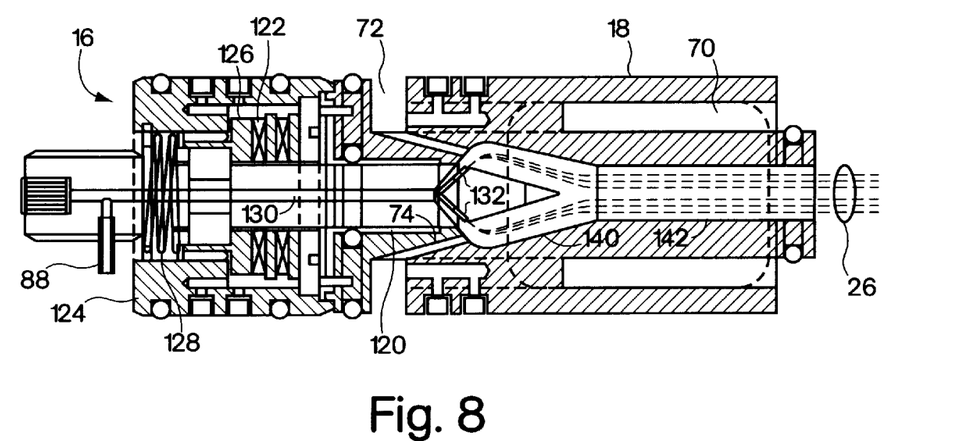
FIG. 8 is a cross-sectional view of the droplet generator used in the therapeutic material delivery system of FIG. 3.

An example of an implementation of the therapeutic material delivery system of the present invention is shown in FIGS. 3–5. Additional details are shown in FIGS. 6–8. Like elements in FIGS. 1–8 have the same reference numerals.

Housing 10 preferably has a lightweight, compact configuration so that the delivery device is portable and handheld. The delivery device may be roughly equivalent in size to a handheld scientific calculator. The housing may, for example, be fabricated of molded plastic. A flexible sliding cover 50 covers an opening 52 when the delivery device is not in use. The opening 52 provides access to a storage area for drying tube assembly 32 and functions as an intake port for entry of ambient air into the gas conditioning assembly 20. A hinged cover 54 provides access to the fluid feed assembly 14 for inserting a container of therapeutic material into the delivery system.

The gas conditioning assembly 20 includes a gas conduit that provides a gas passage from opening 52 through desiccant module 22 and heater 24 to dispersion chamber 18. The desiccant module 22 includes a desiccant material and a dust filter 23. The desiccant module is configured to control the relative humidity of the air passing through the gas conditioning assembly 20 to an upper limit of about 30–50 percent. The transport air heater 24 may include electric heater elements 60 thermally coupled to a heat exchanger 62. As air passes through the heat exchanger 62, it may be heated to a temperature in a range of about 120–175° F. depending on ambient air temperature and relative humidity.

The transport air heater 24 may be controlled by measuring the temperature and relative humidity of the output gas from gas conditioning assembly 20 and adjusting the heater 24 to achieve preset values based on designated droplet size. In particular, a temperature sensor 64 and a relative humidity sensor 66 may be positioned to sense the output of gas conditioning assembly 20. The sensed values may be used to control heater elements 60.

The heated and dried air promotes controlled and rapid drying of the droplets in the aerosol stream. Furthermore, the temperature of the dispersion chamber 18 can be elevated above the level at which bacteria can survive, thereby ensuring the sterility of the device.

After passing through heat exchanger 62, the heated transport air passes through a slotted annular passage 70 (FIG. 5) that surrounds dispersion chamber 18, thereby heating dispersion chamber 18. Furthermore, the structure defining dispersion chamber 18 conducts heat from transport air heater 24 to dispersion chamber 18, thereby further heating the dispersion chamber 18. Thus, dispersion chamber 18 is heated by the gas passing through passage 70 and by conduction from transport air heater 24. Slotted annular passage 70 is connected to a semi-torus or groove manifold 72 which, in turn, is connected through tubes 74 to dispersion chamber 18 adjacent to droplet generator 16. The heated air delivered through tubes 74 to dispersion chamber 18 forms a highly laminar, dried and heated transport gas stream.

In the example of FIGS. 3–8, fluid feed assembly 14 includes a replaceable vial 80 containing a therapeutic solution. The therapeutic solution is a suitable fluid containing a drug or genetic material to be administered to the patient. The vial 80 includes a movable piston 82 for forcing the therapeutic solution from the vial to the droplet generator 16. A hollow needle 86, mounted in a cap 84, is inserted into the elastomeric head of vial 80. The needle 86 is connected by a flexible tube 88 to droplet generator 16. Fluid that is forced from vial 80 by displacement of piston 82 passes through needle 86 and flexible tube 88 to droplet generator 16.

Fluid feed assembly 14 further includes a piston driver 100, as best shown in FIG. 7, for controlled displacement of piston 82. In the illustrated example, piston driver 100 includes a miniature motor 102, a harmonic drive 104 or a reduction gear box, transfer gears 106 and 108 and a lead screw 110. Motor 102 is coupled to harmonic drive 104, and the output of harmonic drive 104 is coupled through gears 106 and 108 to lead screw 110. The lead screw, in turn, is connected to piston 82. When the motor 102 is energized, piston 82 is displaced within vial 80, causing the fluid to be forced through needle and tube 88. Furthermore, piston driver 100 may be reversed to withdraw the fluid from the orifices in the droplet generator and thereby prevent clogging of the droplet generator orifices, when the delivery system is deactivated.

An encoder 112 attached to motor 102 permits sensing of motor rotation and thereby permits sensing of the position of piston 82 in vial 80. The position of piston 82 in vial 80 is indicative of the amount of therapeutic solution delivered to the droplet generator 16.

The fluid feed assembly 14 may further include a vial reader 114 for reading a bar code, a memory module, a magnetic strip or other information carrying device. The bar code or other information carrying device on vial 80 may identify the therapeutic material within vial 80 and may define operating parameters of the delivery device, such as, for example, droplet size and transport air temperature. The outputs of the vial reader 114 may be supplied to a controller as described below.

It will be understood that a variety of different fluid feed systems may be utilized within the scope of the invention. For example, a vial having a fluid containing the therapeutic material may be pressurized with a miniature air compressor. A tube immersed in the fluid carries the fluid from the vial to the droplet generator 16 under control of the pressurized air within the vial. In another approach, a precision miniature pump is connected between the vial and the droplet generator. The pump supplies fluid containing the therapeutic material from the vial to the droplet generator. This approach has the disadvantage that the pump is contaminated with the therapeutic material. In yet another approach, a vial having a piston is affixed to a prepressurized gas accumulator. The gas accumulator displaces the piston and forces fluid containing the therapeutic material from the vial to the droplet generator.

The droplet generator, as best shown in FIG. 8, includes a nozzle 120 and a piezoelectric driver 122. The nozzle 120 and the piezoelectric driver 122 are mounted in a cylindrical housing 124. A coupling element 126 and a spring 128 mechanically couple the piezoelectric driver 122 to nozzle 120. Nozzle 120 includes a passage 130 that interconnects flexible tube 88 to nozzle orifices 132.

In a preferred embodiment, the droplet generator 16 has a modular configuration wherein nozzle 120 is easily replaceable. Replacement of nozzle 120 is required when orifices 132 become clogged or when the nozzle 120 is contaminated with an undesired therapeutic material. In normal use, the nozzle 120 may be replaced after each dose application. Preferably, nozzle 120, flexible tube 88, cap 84 and needle 86 are replaced as a unit.

Orifices 132 discharge fluid into dispersion chamber 18 for dispersion of droplets in the heated transport gas stream. In a preferred embodiment, nozzle 120 has eight equally-spaced orifices. However, any number of orifices may be utilized. The orifices preferably have diameters of 10–50 micrometers, but are not limited to this range. The orifices may be defined by preformed inserts that are mounted in openings in the nozzle. In another approach, a nozzle cap having orifices may be affixed to the nozzle. In other embodiments, the orifices may be defined by multiple machined holes, a porous membrane, a sintered material, a micromesh screen or any other material having orifices.

The piezoelectric driver 122 oscillates nozzle 120 and thereby oscillates the liquid discharge stream emerging from each orifice in nozzle 120. A continuous liquid stream, known as a "ligament", rather than droplets emerges from the nozzle orifices. This approach allows dropletization to take place downstream of the orifices, where the ligaments are intercepted by the transport gas stream. The distance between each orifice 132 and the point of dropletization can be precisely controlled by the oscillation amplitude of piezoelectric driver 122. This allows high speed monosize dropletization to take place within a controlled slipstream jet for optimum dispersion efficiency. The droplet generator firing rate is determined by the nozzle orifice size, desired drop size, frequency of piezoelectric driver 122 and droplet dispersion efficiency. Limits on droplet firing rates are governed by fluid viscosity, density, and surface tension, as well as the droplet-to-droplet interstitial spacing, which if small results in coagulation.

It will be understood that other types of droplet generators may be utilized in the delivery device of the present invention. Examples of suitable droplet generator technologies include those using electrohydrodynamic spray technology, ligament swirl dispersion without a piezoelectric driver and macro-droplet breakup to create small droplets, or any other type of droplet generator. An electrohydrodynamic droplet generator is disclosed in U.S. Pat. No. 5,655,517 issued Aug. 12, 1997 to Coffee.

Droplet dispersion chamber 18 includes a frustoconical upstream portion 140 and a cylindrical downstream portion 142. A tapered tip of nozzle 120 having orifices 132 extends into frustoconical portion 140. Tubes 74, which carry heated air into dispersion chamber 18, terminate at an upstream end of frustoconical portion 140. A pressure sensor 144 (FIG. 1) or a mechanical switching mechanism is preferably attached to the dispersion chamber 18.

The fluid discharge ligament from each orifice 132 of nozzle 120 penetrates into the transport air stream at the point of dropletization. The discharge ligament harmonically oscillates through the flow-induced vibration from the transport air stream. The oscillating ligament distributes the newly-formed monosized droplets in a conical shell geometry which promotes greater volumetric distribution of the droplet aerosol plume. The droplets are accelerated by the momentum of the transport air stream. The preferred angle of approach of the fluid ligament to the transport air stream is between 45° and 90°. At the point of transport air to ligament impact, the center-to-center spacing between droplets then opens from less than 2D, where D is the droplet diameter, at dropletization launch to 4D to 8D as the droplet plume merges into the continuous cross flow transport air stream to form aerosol stream 26

The typical ligament length between orifice 132 and the region of droplet formation is typically about 5D. Typical firing rates for 40 micron droplets are in a range of about 20K to 40K droplets per second. The droplets typically have diameters D that are about twice the diameter of orifice 132. The piezoelectric driver 122 typically operates in a frequency range between about 10 kHz and 45 kHz.

The droplet drying tube assembly 32 is the interface between the delivery system and the patient. The drying tube assembly 32 includes a drying tube 148 and a mouthpiece 150 near the end of the drying tube 148. The mouthpiece 150 is configured to depress the tongue and to promote an open pharyngeal region for good transport of the aerosol stream. As shown in FIG. 3, the drying tube assembly 32 is attached to a pivotable hub 152. The drying tube 32 may be pivoted about hub 152 between an operating position 154 and a storage position 156. In the storage position, drying tube assembly 32 is stored within housing 10. Furthermore, rotation of hub 152 preferably closes dispersion chamber 18, when the drying tube assembly 32 is in the storage position, and prevents contamination of the dispersion chamber. The drying tube assembly 32 can activate electrical and electronic components of the delivery system when it is pivoted to the operating position. The drying tube assembly 32 may screw into hub 152 so that it is easily removable for maintaining cleanliness and so that the system may be used by different patients.

The drying tube 148 may have a fixed length or it may have a telescoping configuration as shown in FIG. 3. The drying tube 148 is preferably made of a thermally insulating material and may be covered with an insulator sleeve to inhibit heat loss from the aerosol stream. In the telescoping configuration, the drying tube 148 includes concentric tubes 148A and 148B that are slidable relative to each other.

Figure 10:
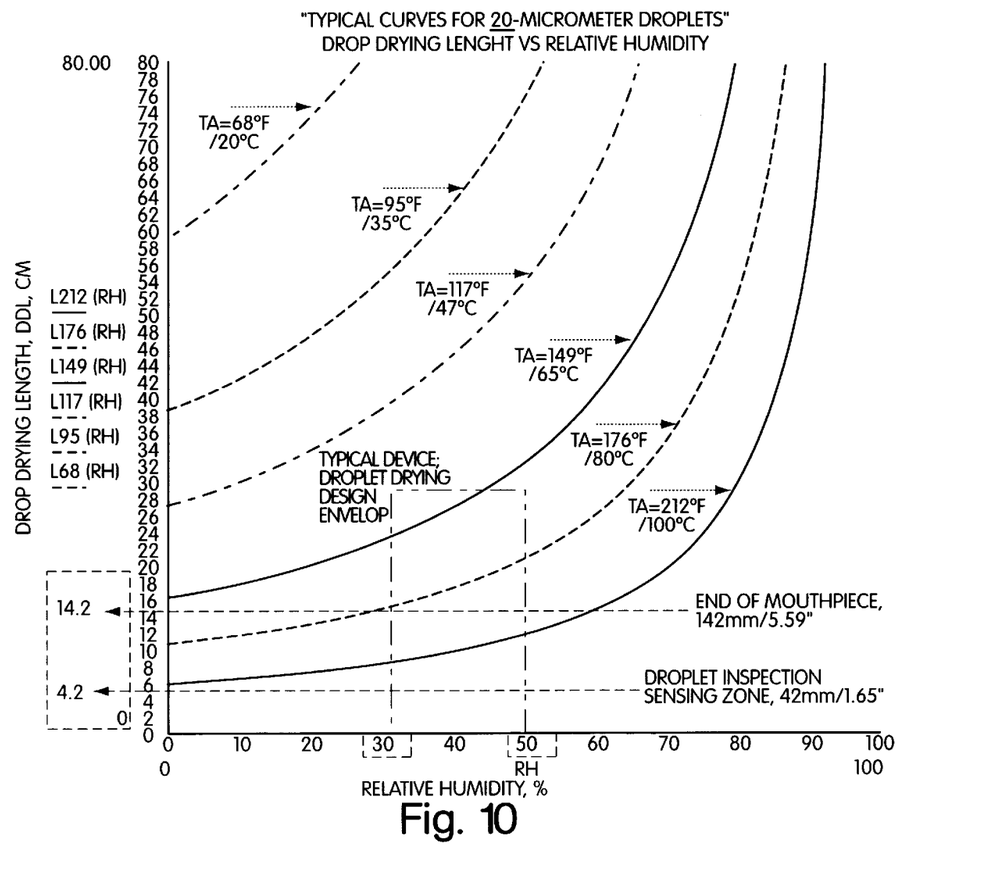
FIG. 10 is a graph of droplet drying length as a function of relative humidity at different temperatures.

The droplets in the aerosol stream are dried, either partially or completely depending on the specified application, by the heated and dried transport air as they pass through drying tube assembly 32. The effectiveness of drying depends on the temperature and relative humidity of the transport air, the droplet size and the length of drying tube assembly 32. A graph of droplet drying length in centimeters as a function relative humidity for different air temperatures for 20 micrometer droplets is shown in FIG. 10. The telescoping drying tube may be adjusted to accommodate different droplet sizes and different transport air temperature and relative humidity. By increasing the drying tube length, the energy required for droplet drying is decreased. The longer the residence time of the droplet in the drying tube, the less the heat energy required for drying droplets of a specified size.

The droplet inspection assembly 30 is preferably configured to optically inspect the aerosol stream 26 between the outlet of dispersion chamber 18 and the inlet of drying tube 32. As shown in FIG. 2, the droplet inspection assembly 30 includes light source 40 for illuminating aerosol stream 26 and light sensor 42 for determining a characteristic of the illuminated aerosol stream. Light sensor 42 supplies a control signal to feedback unit 34 for controlling one or more of fluid feed assembly 14, droplet generator 16 and transport air heater 24, as described in detail below. For example, the feedback unit 34 may vary the amplitude and/or frequency of piezoelectric driver 122 and/or may vary the power supplied to transport air heater 24 in response to the determined characteristic of the aerosol stream. When the delivery device includes an electrohydrodynamic droplet generator, the feedback unit 34 may control electrical charging of comminution sites and/or fluid pumping to comminution sites in the electrohydrodynamic droplet generator. The feedback unit 34 may inhibit operation of the system under certain conditions.

An example of an implementation of the droplet inspection assembly 30 is illustrated in FIGS. 4–6. Optical components associated with generation of a light beam are mounted on a printed circuit board 170, and optical components associated with light sensing are mounted on a printed circuit board 172. The printed circuit boards 170 and 172 are mounted within housing 10 on opposite sides of the aerosol stream 26. Printed circuit boards 170 and 172 are shown in FIG. 6 rotated outwardly from their normal mounting positions.

Light is transmitted through aerosol stream 26 by a light pipe 174 having beveled ends 176. Light pipe 174 includes a bore 178 for passage of aerosol stream 26. Bore 178 preferably has a conical to square conduit transition geometry, so that the aerosol stream will maintain a laminar flow without turbulent edge effect eddies. The light beam is directed through the square portion of bore 178 so as to minimize distortion.

As shown in FIG. 6, optical components of light source 40 and light sensor 42 may be mounted on printed circuit boards 170 and 172, respectively. In the example of FIG. 6, light source 40 includes a laser diode 190 which produces a laser beam 192. The laser beam 192 is directed through beam-expanding transfer lenses 194, 196 and 198 and through aperture 200 to light pipe 174. The light pipe conducts the laser beam through the aerosol stream to the sensing components on printed circuit board 172. In the example of FIG. 6, the sensing components include transfer lenses 210, 212, etc., a beamsplitter 214 and sensors 220. In one example, the sensor 220 may be a photosensor for sensing transmitted light intensity and the sensor 222 may be a linear sensor array for determining droplet size as described below. It will be understood that a variety of different optical configurations may be utilized within the scope of the invention.

The printed circuit boards 170 and 172 preferably include circuit components 230, 232, etc., such as integrated circuits and the like, for controlling operation of the delivery system. For example, component 230 may be a microprocessor for controlling operation of the delivery system. Circuitry for implementing feedback unit 34 (FIG. 1) may be mounted on one or both of printed circuit boards 170 and 172.

A number of different sensing and control functions may be performed by the droplet inspection assembly 30 and the feedback unit 34. The droplet inspection assembly 30 and the feedback unit 34 together perform feedback control of the delivery device. Furthermore, the characteristics of the aerosol stream measured by the droplet inspection assembly 30 may be stored for later analysis and/or for recordkeeping purposes.

The droplet inspection assembly 30 may be utilized to determine and control droplet size in the aerosol stream. In this application, droplet size is determined by inspecting individual droplets. In particular, a linear sensor array having its long dimension optically perpendicular to the aerosol stream may be used to determine particle size. The number of elements in the linear sensor array blocked by a droplet is a measure of droplet size. When the measured droplet size does not meet a predetermined condition, such as being within a prescribed range of diameters, the feedback unit 34 may generate a control signal. The control signal is supplied to the droplet generator for adjusting droplet size within the prescribed range. For example, the oscillation frequency of the piezoelectric driver 122 may be varied to control droplet size. Furthermore, when the droplet size does not meet the predetermined condition, operation of the delivery system can be interrupted or terminated.

The ability to control droplet size is important in controlling the deposition site in the patient's pulmonary system. Larger droplets tend to be deposited within the patient's pharyngeal region, whereas progressively smaller droplets are deposited deeper into the pulmonary system, with the smallest droplets being deposited deep in the patient's lungs. By selection of droplet size and careful control of droplet size in near real time during use of the delivery system, the deposition site is precisely controlled.

Another aspect of the invention is the unique ability to target designated regions of the pulmonary system for site-specific deposition of aerosol droplets containing therapeutic material. This feature is controlled by the inspection assembly and the feedback unit, whereby a droplet size distribution and generation period are predetermined. For example, droplets of 10–13 micrometers will tend to impact and deposit within the pharyngeal/throat region, droplets of 7–9 micrometers deposit within the trachea-bronchus region, and droplets of 1–4 micrometers deposit within the deep lung at the alveolar sac region. The feedback unit can be set manually or programmed directly from reading the bar code or other information carrying device on the vial. By programming the feedback unit, the droplet generator will produce variable narrow spectra of droplets that are targeted for deposition to predetermined pulmonary sites for a predetermined dosing time, thus providing proximal and distal therapy for the entire pulmonary system. In addition, the system can accommodate variances in regional bioavailability as well as comply with prescribed treatment requirements.

Another aspect of the invention is the unique ability to control aerosol droplet size in near real time. This provides this therapeutic material delivery system with unparalleled "payload versatility", which is the ability to deliver varying amounts of therapeutic material over a broad dynamic range using the same delivery system. This is necessary because the new macromolecules and genetic material carriers, such as liposomes, vary widely in required treatment potency from a few micrograms to tens of milligrams per dose. For the new inhalation therapies to accomplish their medical goals, therapeutic droplets delivered to the lungs must be precise and consistent. Currently, there are no new macromolecule drugs which appear to induce a patient's biofeedback mechanism to alert them to a proper therapeutic material dosing. This is why onboard inspection of the therapeutic material droplet aerosol is so critical to ensure the bioavailability efficacy and safe dosimetry of the patient.

In another inspection configuration, a light sensor senses the intensity of light that is transmitted through the aerosol stream. The transmitted light intensity is a function of droplet concentration. By measuring droplet concentration as a function of time, the dose of therapeutic material delivered to the patient can be monitored. When the desired dose has been reached, the droplet generating assembly can be inhibited, thereby preventing further delivery of the aerosol stream. Furthermore, measurement of droplet concentration is indicative of the operating condition of the droplet generator. If one or more of the orifices in the nozzle of the droplet generator become clogged, the droplet concentration decreases. However, provided that some of the orifices remain functional, delivery of therapeutic material can continue. In this case, the delivery time is extended until the prescribed dose has been delivered.

In another inspection configuration, the droplet inspection assembly 30 can be used to determine and/or verify the composition of the therapeutic material by fluorescence analysis. The aerosol stream is illuminated at a wavelength or range of wavelengths selected to stimulate fluorescence emission from the therapeutic material in the droplets. The fluorescence emission from the therapeutic material, typically at one or more wavelengths that are different from the wavelength of the stimulating light beam, are analyzed to determine composition. If the composition differs from the desired composition of the therapeutic material, operation of the delivery device can be inhibited or modified accordingly.

In yet another droplet inspection configuration, the sensor may be an imaging device, such as a CCD camera. The imaging device obtains a high resolution image of the droplets in the aerosol stream and can be used to determine shape as well as droplet size and concentration. The determined characteristics can be used to control operation of the delivery system as described above.

Figure 9:
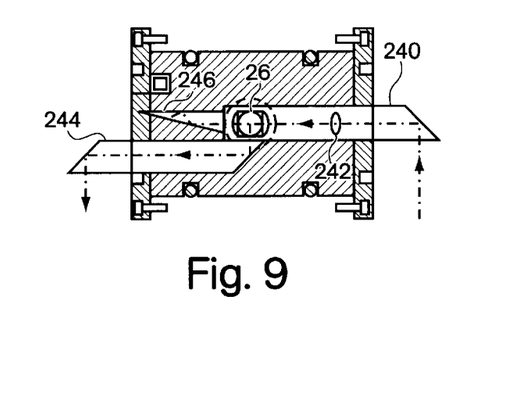
FIG. 9 illustrates an alternate embodiment of the droplet inspection assembly for light scattering measurements.

In still another droplet inspection approach, droplet light scattering is measured. As shown in FIG. 9, a first light pipe 240 directs a light beam 242 through aerosol stream 26. The light beam 242 is intercepted by a light trap 246 after passing through aerosol stream 26. A second light pipe 244 transmits light scattered in a direction perpendicular to both aerosol stream 26 and light beam 242 toward a light sensor. A light scattering measurement, for example, may be used to count light pulses from droplets for concentration measurement and to determine droplet size by the reflected light pulse intensity.

The droplet inspection assembly 30 may be calibrated by measuring each sensor output with no aerosol stream 26 present to obtain a baseline value. Later measurements with the aerosol stream present are then compared to the baseline values. Furthermore, initial baseline values may be established during manufacturing and testing of the delivery system. The system controller may be programmed to measure baseline values each time the delivery system is operated and to compare the measured baseline values with the initial baseline values. A discrepancy may be indicative of a malfunction of the delivery system.

As indicated above, the droplet inspection assembly 30 and the feedback unit 34 may interrupt or terminate operation of the delivery device when a sensed characteristic of the aerosol stream meets a predetermined condition. Also, operation of the delivery device may be interrupted or terminated when the sensed pressure in dispersion chamber 18 exceeds a predetermined level. In each case, the piston driver 100 is preferably reversed so that piston 82 draws fluid back into vial 80 and reduces the risk that the therapeutic solution will dry within the orifices 132 in nozzle 120 and promote clogging.

As indicated above, the delivery device includes a system controller which may, for example, be implemented as a microprocessor. The system controller controls system components such as the fluid feed assembly 14, droplet generator 16, transport air heater 24, droplet inspection assembly 30 and feedback unit 34. The controller receives inputs from various sensors in the delivery system such as for example, pressure sensor 144, temperature sensor 64, relative humidity sensor 66, encoder 112 and light sensor 42. Furthermore, the controller receives programming inputs that define operating parameters for a particular application. The operating parameters may, for example, be received from vial reader 114 (FIG. 7). In other embodiments, the operating parameters may be entered manually or automatically by attaching the delivery system to a programming unit such as a personal computer. In yet another embodiment, the delivery system may be programmed by an onboard memory device such as a read only memory. The controller controls droplet size, dose of therapeutic material, temperature and relative humidity of transport air, and all other parameters of the delivery system.

The delivery system of the present invention may be provided with an indicator 250 (FIG. 3), such as a light emitting diode, an LCD prompting screen and/or a modulated sound device, mounted at the top of housing 10 in a position that is clearly visible to the patient when the delivery system is in use. The indicator 250 may be illuminated and/or sound may be emitted when the delivery system is ready for use and may, for example, remain illuminated and/or sound may be emitted in a modulated fashion until the prescribed dose of therapeutic material has been delivered to the patient.

The delivery system of the present invention may further include a battery pack 260 (FIG. 3) for energizing the components of the delivery device. The battery pack 260 may, for example, be mounted at the bottom and rear of the delivery system, but is not limited to this location. In another configuration, the delivery system includes an AC adapter that may be plugged into a conventional AC outlet for supplying DC power to the delivery system, with proper medical device power isolation safety precautions.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A therapeutic material delivery system comprising:
   a droplet dispersion chamber;
   a droplet generating assembly for generating droplets of a fluid containing a therapeutic material and for supplying said droplets to said dispersion chamber, wherein said droplet generating assembly comprises a droplet generator coupled to said dispersion chamber and a fluid feed assembly for supplying the fluid containing the therapeutic material to said droplet generator at a controlled rate, wherein said droplet generator generates droplets of the fluid containing the therapeutic material and supplies said droplets to said dispersion chamber, wherein said droplet generator comprises a nozzle having one or more orifices for supplying the fluid containing the therapeutic material and a piezoelectric driver for oscillating said nozzle;
   a gas conditioning assembly for supplying heated gas to said dispersion chamber to form a heated transport gas stream, wherein said droplets are dispersed in said transport gas stream in said dispersion chamber to provide an aerosol stream containing said droplets; and
   a droplet drying tube assembly located downstream of said dispersion chamber for controlled drying of said droplets and for supplying said aerosol stream to a patient in response to a negative pressure applied by the patient, wherein said delivery system is breath actuated.

2. A therapeutic material delivery system as defined in claim 1 wherein said gas conditioning assembly comprises a conduit between an inlet port and said dispersion chamber, and a transport gas heater disposed for heating gas passing through said conduit from said inlet port to said dispersion chamber.

3. A therapeutic material delivery system as defined in claim 2 wherein said gas conditioning assembly further comprises a desiccant module disposed in said conduit for absorbing water vapor in the gas passing through said conduit from said inlet port to said dispersion chamber.

4. A therapeutic material delivery system as defined in claim 3 wherein gas conditioning assembly further comprises a filter disposed in said conduit for removing particles in the gas passing through said conduit from said inlet port to said dispersion chamber.

5. A therapeutic material delivery system as defined in claim 2 wherein said dispersion chamber is defined by a structure and wherein said conduit passes through the structure that defines said dispersion chamber, wherein said dispersion chamber is heated by the gas passing through said conduit from said inlet port to said dispersion chamber.

6. A therapeutic material delivery system as defined in claim 2 wherein said dispersion chamber is defined by a structure and wherein said transport gas heater is in thermal contact with the structure that defines said dispersion chamber, wherein said dispersion chamber is heated by said transport gas heater.

7. A therapeutic material delivery system as defined in claim 2 wherein said transport gas heater includes a heating element and a heat exchanger for coupling thermal energy from said heating element to the gas passing through said conduit from said inlet port to said dispersion chamber.

8. A therapeutic material delivery system as defined in claim 7 wherein said gas conditioning assembly further includes means for controlling temperature and relative humidity of the heated gas supplied to said dispersion chamber.

9. A therapeutic material delivery system as defined in claim 8 wherein said means for controlling temperature and relative humidity includes a temperature sensor and a relative humidity sensor disposed for sensing the temperature and relative humidity of the gas supplied to said dispersion chamber and means for controlling said transport gas heater in response to the sensed temperature and relative humidity.

10. A therapeutic material delivery system as defined in claim 1 further including means for heating said dispersion chamber.

11. A therapeutic material delivery system as defined in claim 1 wherein said fluid feed assembly comprises means for holding a vial containing the fluid, said vial having a movable piston for forcing the fluid from the vial to said droplet generator, and a piston driver for controlled displacement of said piston.

12. A therapeutic material delivery system as defined in claim 11 wherein said piston driver comprises a motor coupled to a harmonic drive or a reduction gear box and a lead screw coupled between said harmonic drive or reduction gear box and said piston.

13. A therapeutic material delivery system as defined in claim 12 wherein said piston driver further comprises an encoder coupled to said motor for sensing motor rotation to thereby determine the amount of fluid supplied to said droplet generator.

14. A therapeutic material delivery system as defined in claim 11 wherein said fluid feed assembly further comprises a vial reader for reading an information carrying device on said vial and for supplying information read from said information carrying device for control of the delivery system.

15. A therapeutic material delivery system as defined in claim 1 wherein said fluid feed assembly comprises means for holding a vial containing the fluid and a compressor coupled to said vial for discharging the fluid from the vial to said droplet generator.

16. A therapeutic material delivery system as defined in claim 1 wherein said fluid feed assembly comprises means for holding a vial containing the fluid and a miniature pump for pumping the fluid from the vial to the droplet generator.

17. A therapeutic material delivery system as defined in claim 1 wherein said fluid feed assembly comprises means for holding a vial containing the fluid, said vial having a movable piston for forcing the fluid from the vial to the droplet generator, and a prepressurized device coupled to said piston for displacement of said piston.

18. A therapeutic material delivery system as defined in claim 1 further including a pressure sensor for sensing the pressure in said dispersion chamber and means for inhibiting operation of the droplet generating assembly when the sensed pressure exceeds a predetermined level.

19. A therapeutic material delivery system as defined in claim 1 wherein said nozzle includes one or more inserts which define said one or more orifices.

20. A therapeutic material delivery system as defined in claim 1 wherein said nozzle includes a nozzle cap that defines said one or more orifices.

21. A therapeutic material delivery system as defined in claim 1 wherein said nozzle includes a micromesh screen that defines said one or more orifices.

22. A therapeutic material delivery system as defined in claim 1 wherein said nozzle includes a porous membrane that defines said one or more orifices.

23. A therapeutic material delivery system as defined in claim 1 wherein said nozzle is configured to inject a plurality of ligaments of the fluid containing the therapeutic material into said heated transport gas stream for generation of said droplets.

24. A therapeutic material delivery system as defined in claim 1 wherein said nozzle and said piezoelectric driver have modular constructions that permit said nozzle to easily be replaced.

25. A therapeutic material delivery system as defined in claim 1 wherein said droplet drying tube assembly is pivotable between an operating position in alignment with said dispersion chamber and a storage position.

26. A therapeutic material delivery system as defined in claim 25 wherein drying tube assembly is affixed to a pivotable hub that closes said dispersion chamber when said drying tube assembly is in the storage position.

27. A therapeutic material delivery system as defined in claim 25 wherein said droplet drying tube assembly has a telescoping structure.

28. A therapeutic material delivery system as defined in claim 25 further comprising means for energizing said delivery system when said drying tube assembly is in the operating position and for deenergizing the delivery system when said drying tube assembly is in the storage position.

29. A therapeutic material delivery system as defined in claim 1 further including a compact handheld housing enclosing said dispersion chamber, said droplet generating assembly and said gas conditioning assembly.

30. A therapeutic material delivery system as defined in claim 29 wherein said housing includes a pivoting cover for access to said fluid feed assembly.

31. A therapeutic material delivery system as defined in claim 29 further including an indicator for indicating to the patient that the system is ready for delivery of said aerosol stream.

32. A therapeutic material delivery system as defined in claim 1 wherein said droplet generating assembly includes means for adjusting sizes of said droplets.

33. A therapeutic material delivery system comprising:
a droplet dispersion chamber;
a droplet generating assembly for generating droplets of a fluid containing a therapeutic material and for supplying said droplets to said dispersion chamber;
a gas conditioning assembly for supplying a gas to said dispersion chamber to form a transport gas stream, wherein said droplets are dispersed in said transport gas stream in said dispersion chamber to provide an aerosol stream containing said droplets;
a droplet inspection assembly for determining a characteristic of said aerosol stream; and
a feedback unit responsive to the determined characteristic of said aerosol stream for controlling one or more of said droplet generating assembly and said gas conditioning assembly.

34. A therapeutic material delivery system as defined in claim 33 wherein said droplet inspection assembly includes means for determining the sizes of the droplets in said aerosol stream and wherein said feedback unit includes means for controlling one or more of said droplet generating assembly and said gas conditioning assembly in response to the determined sizes of said droplets.

35. A therapeutic material delivery system as defined in claim 33 wherein said droplet inspection assembly includes means for determining droplet concentration in said aerosol stream and wherein said feedback unit includes means for controlling one or more of said droplet generating assembly and said gas conditioning assembly in response to the determined droplet concentration.

36. A therapeutic material delivery system as defined in claim 33 wherein said droplet inspection assembly includes means for determining a droplet rate of the droplets in said aerosol stream and wherein said feedback unit includes means for controlling one or more of said droplet generating assembly and said gas conditioning assembly in response to the determined droplet rate.

37. A therapeutic material delivery system as defined in claim 33 wherein said droplet inspection assembly includes means for determining a dose quantity of said therapeutic material delivered to the patient and wherein said feedback unit includes means for controlling one or more of said droplet generating assembly and said gas conditioning assembly in response to the determined dose quantity.

38. A therapeutic material delivery system as defined in claim 33 wherein said droplet inspection assembly includes means for determining composition of said therapeutic material.

39. A therapeutic material delivery system as defined in claim 38 wherein said means for determining composition includes means for illuminating the droplets in said aerosol stream with a light beam of a first wavelength and means for sensing fluorescence emissions from said therapeutic material at one or more second wavelengths.

40. A therapeutic material delivery system as defined in claim 33 wherein said droplet inspection assembly includes an image sensor for obtaining an image of said aerosol stream and means for determining said characteristic of said aerosol stream from said image.

41. A therapeutic material delivery system as defined in claim 33 wherein said droplet inspection assembly includes a light source for illuminating said aerosol stream with a light beam and a sensor for sensing light from said aerosol stream.

42. A therapeutic material delivery system as defined in claim 41 wherein said light source and said sensor are located on opposite sides of said aerosol stream.

43. A therapeutic material delivery system as defined in claim 42 wherein said droplet inspection assembly determines the amount of light blockage by said aerosol stream.

44. A therapeutic material delivery system as defined in claim 41 wherein said sensor is located at 90° with respect to said light beam.

45. A therapeutic material delivery system as defined in claim 41 wherein said droplet inspection assembly includes means for determining said characteristic of said aerosol stream from light scattered by said aerosol stream.

46. A therapeutic material delivery system as defined in claim 33 wherein said droplet inspection assembly includes optical components and wherein said optical components are located on a printed circuit board mounted adjacent to said aerosol stream.

47. A therapeutic material delivery system as defined in claim 33 wherein said feedback unit includes means for inhibiting operation of said droplet generating assembly when the determined characteristic meets a predetermined condition.

48. A therapeutic material delivery system as defined in claim 33 wherein said droplet generating assembly comprises a nozzle and a piezoelectric driver and wherein said feedback unit includes means for controlling one or both of the amplitude and frequency of the piezoelectric driver.

49. A therapeutic material delivery system as defined in claim 33 wherein said droplet generating assembly comprises an electrohydrodynamic droplet generator and wherein said feedback unit includes means for controlling one or both of electrical charging of comminution sites and fluid pumping to comminution sites in the electrohydrodynamic droplet generator.

50. A method for delivering a therapeutic material to the pulmonary system of a patient, comprising the steps of:
   heating a gas;
   forming the heated gas into a heated transport gas stream;
   dispersing droplets of a fluid containing a therapeutic material in the heated transport gas stream to form an aerosol stream;
   inspecting the aerosol stream to determine a characteristic of said droplets and controlling the dispersion of said droplets in the fluid in response to the determined characteristic;
   controllably drying said droplets in said aerosol stream; and
   delivering the aerosol stream to the patient after the step of controlled drying thereof, in response to inhalation by the patient.

51. A method as defined in claim 50 wherein the step of dispersing droplets of a fluid includes dispersing droplets of a fluid containing a drug.

52. A method as defined in claim 50 wherein the step of dispersing droplets of a fluid includes dispersing droplets of a fluid containing a genetic material.

53. A method as defined in claim 50 further including the step of controlling the heating of said gas in response to the determined characteristic.

54. A method as defined in claim 50 further including the steps of sensing the temperature and relative humidity of the heated gas and controlling the heating of said gas in response to the determined temperature and relative humidity.

55. A method for delivering a therapeutic material to the pulmonary system of a patient, comprising the steps of:
   providing a transport gas stream;
   generating droplets of a fluid containing a therapeutic material;
   dispersing said droplets in said transport gas stream to form an aerosol stream;
   determining a characteristic of said aerosol stream;
   controlling generation of said aerosol stream in response to the determined characteristic of said aerosol stream.

56. A method as defined in claim 55 wherein the step of determining a characteristic of said aerosol stream includes determining the sizes of the droplets in said aerosol stream and wherein the step of controlling generation of said aerosol stream includes controlling the generation of droplets in response to the determined sizes of said droplets.

57. A method as defined in claim 55 wherein the step of determining a characteristic of said aerosol stream includes determining droplet concentration in said aerosol stream and wherein the step of controlling generation of said aerosol stream includes controlling the generation of droplets in response to the determined droplet concentration.

* * * * *